United States Patent [19]

Kemp

[11] Patent Number: 5,439,862

[45] Date of Patent: Aug. 8, 1995

[54] OLIGOMERIZATION CATALYST AND PROCESS

[76] Inventor: Richard A. Kemp, 11510 Chariot, Stafford, Tex. 77477

[21] Appl. No.: 140,643

[22] Filed: Oct. 21, 1993

[51] Int. Cl.$^6$ .............................................. B01J 31/00
[52] U.S. Cl. .................... 502/121; 502/103; 502/104; 502/122; 502/168; 502/208; 502/215; 502/216
[58] Field of Search ............... 502/103, 104, 121, 122, 502/168, 208, 215, 216

[56]  References Cited

U.S. PATENT DOCUMENTS

| | | |
|---|---|---|
| 3,644,564 | 2/1971 | Van Zwet et al. |
| 3,647,914 | 3/1972 | Glockner et al. |
| 3,647,915 | 3/1972 | Bauer et al. |
| 3,676,523 | 7/1972 | Mason |
| 3,686,351 | 8/1972 | Mason |
| 3,737,475 | 6/1973 | Mason et al. |
| 3,825,615 | 7/1974 | Lutz |
| 4,020,121 | 4/1977 | Kister et al. |
| 4,260,844 | 4/1981 | O'Donnell et al. ............ 585/523 |
| 4,444,904 | 4/1984 | Ruy ................................ 502/162 |
| 4,528,416 | 7/1985 | Lutz ............................... 585/527 |
| 4,822,915 | 4/1989 | Murray |

OTHER PUBLICATIONS

J. Am. Chem. Soc. 1981, 1234–1235 "A Stable Monocyclic Triarylalkoxy P-H Phosphorane, a 10-P-5 Species with an Apical P-H Bond, and Its Conjugate Base, a Phosphoramide" Michael R. Ross and J. C. Martin.

*Primary Examiner*—Asok Pao
*Assistant Examiner*—E. D. Irzinski

[57] ABSTRACT

The present invention relates to a catalyst suitable for oligomerization of olefins which is prepared by a process which comprises reacting a catalyst precursor ligand having a formula

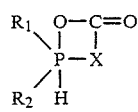

wherein $R_1$ and $R_2$ each independently is an alkyl, alkoxy, aryl, or aryloxy group having from about 1 to about 20 carbon atoms, with the proviso that $R_1$ and $R_2$ are not both aryl, or $R_1$ and $R_2$ together form a divalent hydrocarbon moiety, and X is 1,2-arylene, O—$CH_2$, S—$CH_2$, or Se—$CH_2$ with a deprotonation source, a transition metal compound and a catalyst activator. The invention further relates to an oligomerization process utilizing this catalyst.

12 Claims, No Drawings

OLIGOMERIZATION CATALYST AND PROCESS

FIELD OF THE INVENTION

This invention relates to a process for preparing an oligomerization catalyst and to an oligomerization process utilizing the catalyst.

BACKGROUND OF THE INVENTION

Linear alpha-olefins are compounds having established utility in a variety of applications. For example, linear alpha-olefins having 8 to 20 carbon atoms are key feedstocks in the production of surfactants, plasticizers, synthetic lubricants and polyolefins. High purity alpha-olefins are particularly valuable in the production of low density polyethylene and in the oxo process.

The most successful processes for the production of alpha-olefins to date are those catalyzed by nickel complexes of phosphinecarboxylate ligands and sulfonated ylide/nickel type compounds. While these catalysts are quite active and have good selectivity insofar as the production of alpha-olefins is concerned, the art is continuously searching for olefin oligomerization catalysts which display higher activity and greater alpha-olefin selectivity and allow for a more economical process.

It is known in the prior art to prepare linear alpha-olefins by oligomerizing ethylene at elevated temperature and pressure in a reaction solvent containing a catalytic nickel complex. Particularly useful as catalysts for this process are the complexes prepared as the reaction product of an olefinic nickel compound and a bidentate ligand. Illustrative ethylene oligomerization processes employing a nickel complex catalyst are described in U.S. Pat. No. 3,676,523, U.S. Pat. No. 3,686,351, U.S. Pat. No. 3,737,475, U.S. Pat. No. 3,644,564, U.S. Pat. No. 3,647,914, U.S. Pat. No. 3,647,915, U.S. Pat. No. 3,825,615, U.S. Pat. No. 4,020,121, U.S. Pat. No. 4,260,844, U.S. Pat. No. 4,528,416, and U.S. Pat. No. 4,822,915.

It has now been found that catalysts prepared from a particular five coordinate phosphorus ligand precursor are particularly suitable as oligomerization catalysts. None of the foregoing references contains a catalyst prepared from a five coordinate phosphorus ligand precursor.

SUMMARY OF THE INVENTION

The present invention therefore relates to a catalyst prepared by reacting a catalyst precursor ligand having a formula

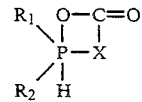

wherein $R_1$ and $R_2$ each independently is an alkyl, alkoxy, aryl, aryloxy group having from about 1 to about 20 carbon atoms, with the proviso that $R_1$ and $R_2$ are not both aryl, or $R_1$ and $R_2$ together form a divalent hydrocarbon moiety having from about 5 to about 40 carbon atoms, and X is a 1,2-arylene, O—$CH_2$, S—$CH_2$, or Se—$CH_2$ group, with a deprotonation source, a transition metal compound and a catalyst activator. The invention further relates to an oligomerization process utilizing this catalyst.

DESCRIPTION OF THE PREFERRED EMBODIMENTS

Oligomers are addition products which contain two or more of monomer units, but not as many units as the relatively high molecular weight addition products which are referred to as polymers. The catalyst of the present invention is particularly adapted for the production of linear mono-olefinic oligomers of ethylene containing from 2 to about 20 monomer units (i.e., from about 4 to about 40 carbon atoms).

Olefins suitable for use in the oligomerization process of the present invention are $C_2$ to $C_{20}$ olefins, particularly $C_2$ to $C_{10}$ olefins, such as, for example, ethylene, propylene, etc. These olefins are oligomerized to an oligomer product stream containing linear alpha-olefins and olefin oligomers. When ethylene is used as the feed for the oligomerization process, a high proportion of linear, alpha olefins is produced.

The catalysts of the present invention can be characterized as transition metal complexes comprising an atom of a transition metal chelated with a ligand derived from a five coordinate phosphorus compound, i.e., a phosphorane, having a formula

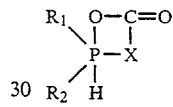

wherein $R_1$ and $R_2$ each independently are alkyl, alkoxy, aryl, or aryloxy groups having from about 1 to about 20 carbon atoms, with the proviso that $R_1$ and $R_2$ are not both aryl, or $R_1$ and $R_2$ together form a divalent hydrocarbon moiety having from about 5 to about 40 carbon atoms, and X is a 1,2-arylene, O—$CH_2$, S—$CH_2$, or Se—$CH_2$ group, with a deprotonation source, a transition metal compound and a catalyst activator. It is understood that the terms alkyl, alkoxy, aryl, aryloxy, 1,2-arylene, O—$CH_2$, S—$CH_2$ and Se—$CH_2$ groups can have any number of substituents which do not interfere with the reaction. As used herein "alkyl" also includes cycloalkyl. Suitable substituents include cyclopentyl, cyclohexyl, hexyl, pentyl, adamantyl, and the like, with cyclopentyl, cyclohexyl and adamantyl being preferred. The divalent hydrocarbon moiety which can be formed by $R_1$ and $R_2$ together is preferably a ring which contains at least four members. The ring formed by $R_1$ and $R_2$ may contain heteroatoms such as nitrogen (N), oxygen (O), or sulfur (S). The ring formed by $R_1$ and $R_2$ may also be part of another ring system or attached to another ring system. In a preferred embodiment, the divalent hydrocarbon moiety formed by $R_1$ and $R_2$ together is a ring containing five or six members.

Suitable alkyl groups in the above formula include ethyl, propyl, butyl, pentyl, hexyl, heptyl, octyl, decyl, dodecyl, etc., and the like, with hexyl, octyl, decyl, dodecyl being preferred. Suitable alkoxy groups in the above formula include ethoxy, butoxy, pentoxy, heptoxy, decyloxy, dodecyloxy, etc., and the like, with butoxy being preferred. Suitable aryl groups include phenyl, tolyl, xylenyl, methoxy phenyl, ethyl phenyl, chlorophenyl, mesityl, etc., and the like, with phenyl, tolyl, and mesityl being preferred. Suitable aryloxy groups include phenoxy, methyl-substituted phenoxy, dimethyl-substituted phenoxy, and halo-substituted phenoxy, etc., and the like, with phenoxy and methyl-substituted phenoxy being preferred.

Particularly suitable phosphorane ligands include compounds having the following formulas:

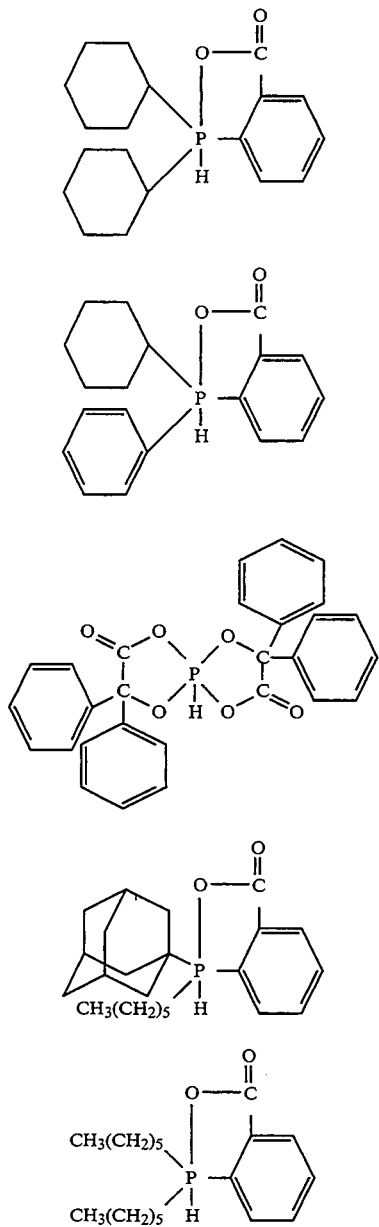

The phosphorane ligand cannot chelate to the transition metal to form a catalyst without first removing the proton attached to the phosphorus atom. Thus, a deprotonation source is required to form the catalyst. Upon deprotonation, the phosphorane converts to a form capable of chelating to the transition metal, i.e., the ring containing the COO⁻ moiety opens up to form an acyclic phosphine/carboxylate ion. The deprotonation source is typically a strong base. Suitable deprotonation sources include sodium hydroxide, potassium hydroxide, alkali metals, alkyl metal reagents such as, for example, butyllithium, and the like, and mixtures thereof. The amount of deprotonation source utilized is typically in the range of from about 0.5 to about 5, preferably in the range of from about 1 to about 1.5, on a molar basis when compared with the amount of phosphorus.

The transition metal compound suitable for use in the catalyst of the present invention can be an organometallic compound, an organic salt, or an inorganic salt wherein the transition metal is selected from the group consisting of nickel, chromium, cobalt, iron, copper, and mixtures thereof. The transition metals are preferably in the following transition states: nickel—0 or 2; chromium, cobalt, and iron—0, 1, 2 or 3; and copper—0, 1 or 2. Where the compound is a salt, the hydrated form is preferred. Metal salts are preferred, particularly the halides, sulfonates, benzenesulfonates, and tetrafluoroborates. Useful metal compounds are the chlorides, bromides, iodides, fluorides, hydroxides, carbonates, chlorates, ferrocyanides, sulfates, hexafluorosilicates, trifluoromethanesulfonates, nitrates, sulfides, selenides, silicides, cyanides, chromates, phenoxides, dimethyldithiocarbamates, hexafluoroacetylacetonates, molybdates, phosphates, oxides, stannates, sulfamates, thiocyanates, cyanates, titanates, tungstates, cyclopentadienides, formates, acetates, hydroxyacetates, propionates, hexanoates, oxalates, benzoates, cyclohexanebutyrates, naphthenates, citrates, dimethylgloximes, acetylacetimides, phthalocyanines, and bis-cyclooctadienes. The nickel salts, particularly those of sulfonate, tetrafluoroborate, and chloride hexahydrate, are preferred. Nickel typically gives the most active catalysts followed by chromium, copper, cobalt, and iron. Mixtures of the various transition metal compounds can be used. In a preferred embodiment, the transition metal compound is a nickel compound.

Specific examples of useful transition metal compounds are NiCl$_2$.6H$_2$O, Ni(BF$_4$)$_2$.6H$_2$O, NiSO$_4$.6H$_2$O, NiBr$_2$.xH$_2$O, Ni(II)acetylacetonate, NiCl$_2$.dimethoxyethane, Ni(OH)$_2$, hexa-amminenickel (II) chloride, nickel benzoate, nickel fluoride.4H$_2$O, nickel tosylate.6-H$_2$O, nickel acetate-4H$_2$O, chromium (III) chloride.6-H$_2$O, chromium(II) chloride, cupric chloride.2H$_2$O, FeCl$_2$.4H$_2$O, and cobalt(II) acetate.4H$_2$O, with NiCl$_2$.6H$_2$O and nickel acetate.4H$_2$O being preferred.

The molar ratio of transition metal to ligand used in catalyst preparation is preferably at least about 1:1, i.e., the transition metal is present in equimolar amount or in molar excess. In the preparation of catalyst complexes from a transition metal salt, a ligand and a reducing agent, the molar ratio of transition metal salt to ligand is suitably in the range of from about 0.8:1 to about 5:1 with molar ratios of about 1:1 to about 3:1 being preferred and ratios of about 1:1 being particularly preferred. In these preparations, the deprotonation source is suitably present in equimolar amounts or molar excess relative to the transition metal salt.

The transition metal catalyst is suitably employed as an unsupported material. In certain modifications, the transition metal catalyst can be supported on an inorganic, solid catalyst carrier which is normally solid under reaction conditions and is heterogeneous, i.e., substantially insoluble in the reaction medium. Illustrative of suitable inorganic, solid catalyst carriers are inorganic acidic oxides such as alumina and inorganic materials known as refractory oxides.

When the catalyst composition is supported, the proportion of catalyst composition to carrier is not critical. In general, proportions of catalyst composition in the range of from about 0.01 percent by weight to about 70 percent by weight, basis the catalyst carrier, are satisfactory, with amounts in the range of from about 0.1 percent by weight to about 20 percent by weight, basis the catalyst carrier, being preferred.

The oligomerization catalyst also contains a catalyst activator or reducing agent. The catalyst activator can be any reagent capable of activating the catalyst under oligomerization conditions. The activator can be selected from among the activators which are well known in the art of polymerization or oligomerization. Preferred catalyst activators are reagents considered to be capable of transferring a hydride or an alkyl, alkenyl, alkynyl, or aryl group from itself to the metal/ligand complex formed by the reaction of the metal salt with the ligand and bonding the group to the transition metal, said activator being present in an amount sufficient to activate the catalyst. Where the transition metal compound already has a hydride or an alkyl, alkenyl, alkynyl, or aryl group bonded to the transition metal and the metal is in the zero oxidation state, a catalyst activator is not required. Suitable activators are borohydrides, aryl boranes, borane ($BH_3$), mono-, di-, and trialkyl boranes, aryl borates, tri and tetra coordinate organoaluminum compounds, aluminum hydrides, tri and tetra alkyl boron compounds, organozinc compounds, and mixtures thereof. The borohydrides can be alkali metal borohydrides, quaternary ammonium borohydrides where the ammonium cation is $R_4N^+$, each R being alike or different and selected from the group consisting of hydrogen and alkyl radicals having 1 to 10 carbon atoms; and alkali metal alkoxyborohydrides, phenoxyborohydrides, or amidoborohydrides, wherein there are 1 to 3 alkoxy, phenoxy, or amido group and each has 1 to 10 carbon atoms. The aryl borane compounds can have 1 to 3 aromatic rings and the aryl borates can have 1 to 4 aromatic rings. All of the various aryl, alkyl or alkoxy groups can be substituted or unsubstituted. Mixtures of the various boron compounds can also be used.

Examples of boron compounds which can be used as activators include sodium borohydride, potassium borohydride, lithium borohydride, sodium trimethylborohydride, potassium tripropoxy-borohydride, tetramethylammoniumborohydride, triphenylborane, sodium tetraphenylborate, lithium tetraphenylborate, lithium hydrido tris(1-pyrazol)borate, potassium dihydro bis(1-pyrazol)borate, lithium triethylborohydride, lithium tri-sec-butylborohydride, potassium tri-sec-butylborohydride, sodium cyanoborohydride, zinc borohydride, bis(triphenylphosphine) copper (I) borohydride, potassium tetraphenylborate, lithium phenyltriethylborate, lithium phenyltrimethoxyborate, sodium methoxytriphenylborate, sodium diethylaminotriphenylborate, and sodium hydroxytriphenylborate. In general, boranes derived from olefin hydroboration are useful. These boranes can be $BH_3$, triethylborane, dicyclohexylborane, trihexylborane, diethylborane, ethylborane, 9-borabicyclononane[3.3.1]nonane, tricyclohexylborane, and catecholborane. Largely because of commercial availability, alkali metal borohydrides are preferred, with sodium borohydride being especially preferred.

When preparing the catalyst, the molar ratio of catalyst activator to transition metal salt is at least about 1:1. There does not appear to be fan upper limit on the activator/transition metal salt, but for economic reasons, it is preferred that the molar ratio not exceed about 15:1. The preferred molar ratio of catalyst activator to transition metal salt is usually between about 1:1 and about 10:1. A ratio of about 2:1 is especially preferred.

The catalyst composition of the present invention is suitably prepared by contacting the catalyst precursors, i.e., the transition metal salt, preferably a nickel salt, the ligand precursor, and the catalyst activator/reducing agent, preferably a boron hydride, in a polar organic diluent or solvent, e.g., polar organic diluents or solvents employed for the oligomerization process which are not reduced by the boron hydride reducing agent. In a preferred modification, the solvent, the nickel salt and the phosphorane ligand are contacted in the presence of the olefin feed before the addition of the boron hydride reducing agent. Generally, the catalyst components are contacted under 10 psig to about 1500 psig of olefin.

The catalyst is generally prepared at temperatures of about 0° C. to about 50° C., although substantially ambient temperatures, e.g., about 10° C. to about 30° C., are preferred. Contact times of about 5 minutes to about 1 hour are generally satisfactory.

The olefin feed, preferably ethylene, is contacted with the catalyst composition in the liquid phase in the absence or presence of a reaction solvent or diluent which is liquid at reaction temperature. In a preferred embodiment, the reaction takes place in the presence of a polar organic solvent or diluent. When present, amounts of diluent or solvent of up to about 30 liters per mole of olefin are satisfactorily employed. Generally, the concentration of the catalyst, calculated as nickel metal, in the solvent or diluent is at least about 0.0001 molar (M), preferably in the range of from about 0.001M to about 0.01M.

Suitable solvents are nonpolar organic solvents such as aliphatic hydrocarbons, e.g., alkanes, including cycloalkanes of from 5 to about 20 carbon atoms, such as cyclopentane, cyclohexane, isohexane, heptene, isooctane, decane, and eicosane; halo-alkanes, e.g., ethylene dichloride, hexachloroethane, 1,4-dichlorobutane; halocyclo-alkanes, e.g., chlorotoluene and xylene; and haloaromatics such as chlorobenzene and hexafluorobenzene.

Other suitable solvents or diluents are polar organic compounds containing atoms such as oxygen, sulfur, nitrogen and phosphorus incorporated in functional groups such as hydroxy, alkoxy, aryloxy, carbalkoxy, alkanoyloxy, cyano, amino, alkylamino, dialkylamine, amide, N-alkylamide, N,N-dialkylamide, sulfonylalkyl and like functional groups. Illustrative oxygenated organic solvents are fully esterified alkanes such as glycerol triacetate, tetraacyl esters of erythritol, diethylene glycol diacetate; monoesters such as ethyl acetate, butyl propionate and phenyl acetate; cycloalkyl ethers, e.g., dioxane, tetrahydrofuran, and tetrahydropyran; acyclic alkyl ethers, e.g., dimethoxyethane, diethylene glycol, dimethyl ether and dibutyl ether; aromatic ethers such as anisole, 1,4-dimethoxybenzene and p-methoxytoluene; aliphatic alcohols such as methanol, trifluoroethanol, hexafluoroethanol, trifluoropropanol, sec-butanol, perfluorobutanol, octanol, dodecanol, cycloalkanols, e.g., cyclopentanol and cyclohexanol; polyhydric acyclic hydroxyalkanes such as glycerol and trimethylene glycol, alkanediols having 2 to about 10 carbon atoms such as ethylene glycol, propylene glycol, 1,4-butanediol and 2,5-hexanediol; phenols such as cresol, p-chlorophenol, m-bromophenol, 2,6-dimethylphenol, p-methoxyphenol, 2,4-dichlorophenol; and alkylene carbonates such as ethylene carbonate, propylene carbonate and butylene carbonate. Illustrative nitrogen-containing organic solvents are nitriles, e.g., acetonitrile and propionitrile; amines, e.g., butylamine, dibutylamine, trihexylamine, N-methylpyrolidine, N-methylpiperidine, and aniline: N,N- dialkylamides, e.g., N,N-dimethylformamide and N,N-dimethylacetamine. Illustrative sulfur-containing solvents are sulfolane and dimethylsulfoxide, and illustrative phosphorus-containing solvents are trialkylphosphates, e.g., trimethylphosphate, triethylphosphate and tributylphosphate, and hexaalkylphosphoramides such as, for example, hexamethylphosphoramide, Preferred reaction diluents and solvents are polar organic solvents, particularly oxygenated organic solvents. Especially preferred are alkanediols having 2 to 6 carbon atoms such as, for example, ethylene glycol, propylene glycol, 1,2-butanediol, 1,4-butanediol and 2,5-hexanediol.

Polar organic solvents and diluents are preferred for use in the oligomerization process because the oligomerization product mixture is essentially insoluble in such solvents and diluents. For example, when a polar organic solvent such as an alkanediol is employed, a two-phase reaction mixture is formed, i.e., one phase comprising the olefin oligomerization product mixture, i.e., the alpha-olefins, and a second phase comprising the transition metal salt and the reaction solvent or diluent. Where a two phase reaction product is formed, the olefin oligomerization product phase is separated and the catalyst containing diluent or solvent phase is utilized for further olefin oligomerization. Polar organic solvents are also preferred in part because the same solvents are employed in catalyst preparation as previously indicated.

The oligomerization process can be practiced according to methods and under conditions which are known in the prior art such as, for example, the methods described in U.S. Pat. No. 3,644,564, U.S. Pat. No. 3,647,914, U.S. Pat. Nos. 3,647,915, 3,676,523, U.S. Pat. No. 3,686,351 and U.S. Pat. No. 3,825,615, the content of which are incorporated herein by reference. The precise method of establishing olefin/catalyst contact during the oligomerization reaction is not critical. Very suitably, a mixture of the catalyst and solvent is prepared and charged to an autoclave or similar pressure reactor.

The oligomerization process is typically carried out at temperatures in the range of from about 0° C. to about 200° C. Preferred temperatures are in the range of from about 30° C. to about 140° C., and particularly preferred temperatures are in the range of from about 60° C. to about 130°. The process is typically carried out at pressures in the range of from about atmospheric pressure to about 5000 psig. Preferred pressures are in the range of from about 400 psig to about 2000 psig. These pressures are the pressures at which the ethylene feed is introduced into the reactor, and at which the reactor is maintained.

Typical catalyst concentrations are in the range of from about 5 parts per million to about 10,000 parts per million by weight of transition metal. Preferred catalyst concentrations are in the range of from about 10 parts per million to about 1,000 parts per million by weight of transition metal, with a range of from about 15 parts per million to about 300 parts per million being particularly preferred.

The oligomerization products are separated and recovered from the reaction mixture by conventional methods such as fractional distillation, selective extraction, adsorption and the like. The reaction solvent, catalyst and any unreacted olefin can be recycled for further utilization.

During the oligomerization process, olefin is converted to dimer, trimer, tetramer, and like higher oligomers with polymers being observed on certain occasions. The product mixture is characterized by a high proportion of linear alpha-olefin products when ethylene is utilized as the olefin reactant.

The olefin oligomer products prepared are materials of established utility and many are chemicals of commerce. The products are converted by conventional "Oxo" process to aldehydes which are hydrogenated with conventional catalysts to the corresponding alcohols. Alternatively, the product olefins are converted to secondary alcohols by sulfuric acid-catalyzed hydration. The $C_{12}$–$C_{20}$ alcohols thereby produced can be ethoxylated by reaction with ethylene oxide in the presence of a basic catalyst, e.g., sodium or potassium hydroxide, to form conventional detergents, and the lower molecular weight alcohols are esterified by reaction with polybasic acids, e.g., phthalic acid, to form plasticizers for polyvinyl chloride.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the present invention as defined by the specification and claims.

The invention is further described with reference to the following examples, which are intended to illustrate certain aspects of the invention, without limiting its broader scope.

ILLUSTRATIVE EMBODIMENTS

The catalyst preparations described below were carried out in an inert atmosphere using standard air-sensitive techniques. Reagents were procured commercially and used without further purification. Solvents were dried and distilled prior to use when appropriate.

EXAMPLE 1

In a nitrogen-purged 500 milliliter flask o-fluorobenzoic acid (7.01 grams, 50 millimoles) was added along with 100 milliliters of anhydrous diethyl ether. The flask was cooled to −78° C. and n-butyllithium (34 milliliters/1.6M in hexane, 54.4 millimoles) was slowly added to form the lithium o-fluorobenzoate. The white precipitate was allowed to warm to room temperature (slurry 1). In a separate 250 milliliter flask purged with nitrogen was added dicyclohexylphosphine (9.91 grams, 50 millimoles) along with 100 milliliters of anhydrous diethyl ether. This solution was cooled to −78° C. and n-butyllithium (36 milliliters/1.6M in hexane, 57.6 millimoles) was added dropwise. The solution was allowed to warm slowly to room temperature, whereupon it turned bright yellow near −10° C. (slurry 2). The yellow chemiluminescent phosphide was allowed to stir at room temperature for approximately 1–2 hours. Slurry 1 was recooled to −78° C. and slurry 2 was added via cannulus over 8–10 minutes. The solution was allowed to warm to room temperature overnight whereupon it assumed a dark red/rust color. The solution was then filtered and 250 milliliters of degassed deionized water was added to extract the anion. Initially upon water addition, the solution became greenish, then more yellow as more water was added. The layers were separated in a separatory funnel and the organic phase was back-extracted with two 75 milliliter portions of water. The water layers were combined and acidified to pH 3 with diluted hydrochloric acid. An off-white precipitate forms which can be isolated by filtration, water-washing, and drying at 30°–90° C. for several hours. Isolated yield of air- and water-stable 1,1-dicyclohexyl-3-oxo[3H-2,1-benzoxaphosphole] was 10.8 grams, a 68% yield.

The catalyst solution was prepared by adding the phosphorane prepared above (0.159 grams, 0.50 millimoles), $NiCl_2 \cdot 6H_2O$ (0.028 grams, 0.50 millimoles) in 175 grams of 1,4-butanediol. This solution was stirred for approximately 15 minutes under 30 bar ethylene pressure. The catalyst is activated by adding a solution of $NaBH_4$ (0.053 grams, 1.40 millimoles) in 25 grams of 1,4-butanediol. The reactor is then raised to a temperature of 90° C. and a pressure of 1300 psig. Ethylene was then fed on demand as the pressure in the reactor decreases from conversion of the gaseous ethylene into less volatile olefins. A total of 60 grams of ethylene oligomer were produced. The resulting olefin stream was immiscible with the 1,4-butanediol and was separated and analyzed by using a Hewlett Packard Model 5880A gas chromatograph using a DB-1 capillary column. The results are presented in Table I.

EXAMPLE 2

Example 2 was carried out using the procedures set forth in Example 1 except that the starting phosphine was cyclohexylphenylphosphine rather than dicyclohexylphosphine. The resulting phosphorane was (±) 1,1-cyclohexylphenyl-3-oxo[3H-2,1-benzoxaphosphole].

The catalyst solution was prepared as in Example 1 above, and the oligomerization reaction was also carried out as in Example 1 above. The results are presented in Table I.

COMPARATIVE EXAMPLE A

Comparative Example A was carried out in a manner similar to Example 1 except that the phosphine ligand used was bis(catecholato)phosphorane, i.e.,

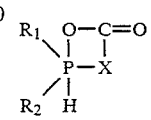

which was prepared by the following literature procedure. (A. Munoz, M. Sanchez, M. Koenig, and R. Wolf, *Bull. Chim. Soc. Fr.*, 2193 (1974)). The results are presented in Table I.

COMPARATIVE EXAMPLE B

Comparative Example B was carried out in a manner similar to Example 1 except that the phosphine ligand used was cyclenphosphorane, i.e.,

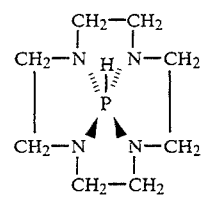

which was prepared by the following literature procedure. (T. J. Atkins and J. E. Richman, *Tetrahedron Letters*, 5149 (1978)). The results are presented in Table I.

TABLE I

| | Ethylene Uptake (g $C_2$=/lcat/hr) | Branched In $C_{12}$ Fraction (%) | Internals In $C_{12}$ Fraction (%) | Alpha-$C_{12}$ Olefin Content (%) |
|---|---|---|---|---|
| Example 1 | 365 | 1.6 | 0.5 | 97.9 |
| Example 2 | 312 | 1.2 | 0.5 | 98.3 |
| Comparative Example A | 0 | — | — | — |
| Comparative Example B | 0 | — | — | — |

As can be seen in Table I, phosphorane ligand precursors having the formula

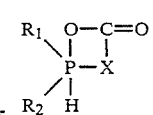

with $R_1$, $R_2$ and X being as hereinbefore defined, are active for oligomerization and provide for alpha olefin oligomers of very high purity, as can be seen by the low amounts of branched and internal olefin impurities. Phosphorane ligands containing P—H bonds which do not possess the above formula are inactive for olefin oligomerization reactions (Comparative Examples A and B), thus showing that a P—H bond in and of itself is not sufficient to provide an active catalyst upon deprotonation and reaction with a metal source.

What is claimed is:

1. A catalyst suitable for oligomerization which is prepared by a process which comprises reacting a catalyst precursor ligand having a formula

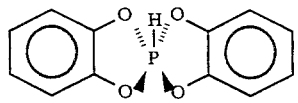

wherein $R_1$ and $R_2$ each independently is an alkyl, alkoxy, aryl, or aryloxy group having from about 1 to about 20 carbon atoms, with the proviso that $R_1$ and $R_2$ are not both aryl, or $R_1$ and $R_2$ together form a divalent hydrocarbon moiety, and X is 1,2-arylene, O—$CH_2$, S—$CH_2$, or Se—$CH_2$, with a deprotonation source, a transition metal compound wherein the transition metal is selected from the group consisting of nickel, chromium, cobalt, iron, copper, and mixtures thereof, and a catalyst activator, wherein the molar ratio of catalyst activator to transition metal compound is at least about 1:1.

2. The catalyst of claim 1 wherein said catalyst precursor ligand has a formula

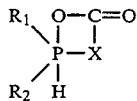

wherein $R_1$ is an alkyl, alkoxy or aryloxy group having from about 1 to about 20 carbon atoms and $R_2$ is an alkyl, alkoxy or aryloxy group having from about 1 to about 20 carbon atoms, and X is 1,2-arylene, $O-CH_2$, $S-CH_2$, or $Se-CH_2$.

3. The catalyst of claim 1 wherein said catalyst precursor ligand has a formula

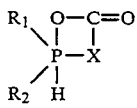

wherein $R_1$ is an alkyl, alkoxy or aryloxy group having from about 1 to about 20 carbon atoms and $R_2$ is an aryl group, and X is 1,2-arylene, $O-CH_2$, $S-CH_2$, or $Se-CH_2$.

4. The catalyst of claim 1 wherein said catalyst precursor ligand has a formula

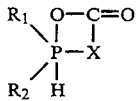

wherein $R_1$ is an alkyl, alkoxy or aryloxy group having from about 1 to about 10 carbon atoms and $R_2$ is an alkyl, alkoxy, aryl or aryloxy group having from about 1 to about 10 carbon atoms, and X is 1,2-arylene, $O-CH_2$, $S-CH_2$, or $Se-CH_2$.

5. The catalyst of claim 1 wherein said catalyst precursor ligand has a formula

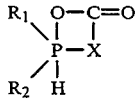

wherein $R_1$ is an alkyl, alkoxy or aryloxy group having from about 1 to about 20 carbon atoms and $R_2$ is an alkyl, alkoxy, aryl or aryloxy group having from about 1 to about 20 carbon atoms, and X is 1,2-arylene or $O-CH_2$.

6. The catalyst of claim 1 wherein said catalyst precursor ligand has a formula

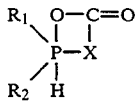

wherein $R_1$ and $R_2$ together form a ring having from about 4 to about 10 members.

7. The catalyst of claim 6 wherein said catalyst precursor ligand has a formula

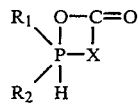

wherein $R_1$ and $R_2$ together form a ring having from about 4 to about 6 members.

8. The catalyst of claim 1 wherein said catalyst precursor ligand is selected from the group consisting of

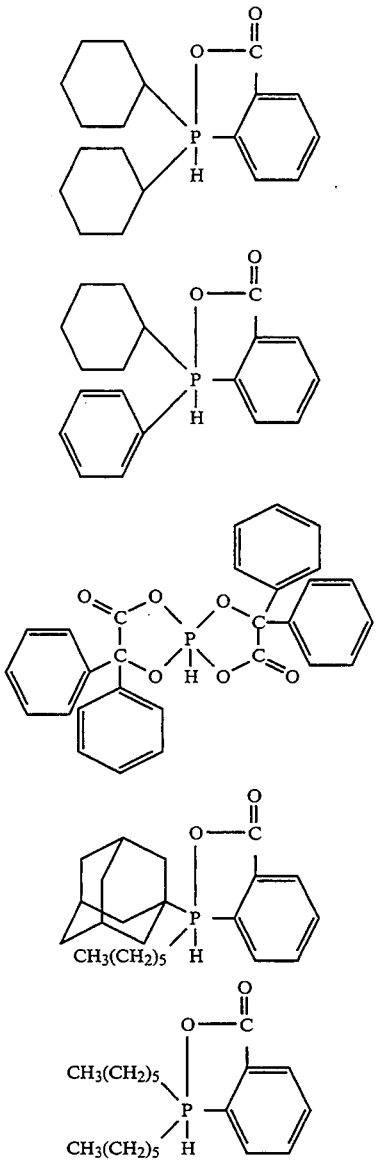

and mixtures thereof.

9. The catalyst of claim 1 wherein said deprotonation source is selected from the group consisting of sodium hydroxide, potassium hydroxide, alkali metals, alkyl metals and mixtures thereof.

10. The catalyst of claim 1 wherein said transition metal compound is selected from the group consisting of nickel salts, chromium salts, cobalt salts, iron salts, copper salts and mixtures thereof.

11. The catalyst of claim 10 wherein said transition metal is a nickel salt.

12. The catalyst of claim 1 wherein said catalyst activator is selected from the group consisting of borohydrides, aryl boranes, borane ($BH_3$), mono-, di-, and trialkyl boranes, aryl borates, tri and tetra coordinate organoaluminum compounds, aluminum hydrides, tri and tetra alkyl boron compounds, organozinc compounds, and mixtures thereof.

* * * * *

UNITED STATES PATENT AND TRADEMARK OFFICE
CERTIFICATE OF CORRECTION

PATENT NO. : 5,439,862
DATED : August 8, 1995
INVENTOR(S) : Richard A. Kemp

It is certified that error appears in the above-identified patent and that said Letters Patent is hereby corrected as shown below:

On the cover page of the patent after line [76] and before line [21] insert:

[73] Assignee: Shell Oil Company, Houston, Tex.

Signed and Sealed this

Fourteenth Day of November, 1995

Attest:

BRUCE LEHMAN

Attesting Officer

Commissioner of Patents and Trademarks